US006183825B1

(12) United States Patent
Crook

(10) Patent No.: US 6,183,825 B1
(45) Date of Patent: Feb. 6, 2001

(54) PROTECTIVE MATERIAL FOR PREVENTING MICROBIOLOGICALLY-INFLUENCED CORROSION IN BURIED CONDUITS

(75) Inventor: John A. Crook, Birmingham, AL (US)

(73) Assignee: Fulton Enterprises, Inc., Birmingham, AL (US)

(*) Notice: Under 35 U.S.C. 154(b), the term of this patent shall be extended for 0 days.

(21) Appl. No.: 09/223,603

(22) Filed: Dec. 30, 1998

Related U.S. Application Data

(63) Continuation-in-part of application No. 08/669,111, filed on Jun. 24, 1996.

(51) Int. Cl.⁷ .................................................. A01N 25/34
(52) U.S. Cl. ..................... 428/34.7; 428/36.91; 428/516; 424/411; 424/412; 138/141; 138/146; 138/DIG. 6
(58) Field of Search .................................. 428/500, 516, 428/34.6, 34.7, 36.9, 36.91, 377; 523/122; 424/411, 412; 138/141, 146, 145, 172, DIG. 6

(56) References Cited

U.S. PATENT DOCUMENTS

| | | |
|---|---|---|
| 2,937,665 | 5/1960 | Kennedy . |
| 3,024,153 | 3/1962 | Kennedy . |
| 3,033,724 | 5/1962 | Stokes . |
| 3,157,204 | 11/1964 | Phillips . |
| 3,223,571 | 12/1965 | Straughan . |
| 3,425,954 | 2/1969 | Ruzevick et al. . |
| 3,469,002 | 9/1969 | Moyer . |
| 3,565,747 | 2/1971 | Vincent et al. . |
| 3,687,765 | 8/1972 | MacLean et al. . |
| 3,692,619 | 9/1972 | Wedekind et al. . |
| 3,877,490 | 4/1975 | Tsubouchi et al. . |
| 4,035,546 | 7/1977 | Ruppert, Jr. . |
| 4,051,066 | 9/1977 | Miksic et al. . |
| 4,211,595 | 7/1980 | Samour . |
| 4,213,486 | 7/1980 | Samour et al. . |
| 4,254,165 | 3/1981 | Phelps et al. . |
| 4,290,912 | 9/1981 | Boerwinkle et al. . |
| 4,321,297 | 3/1982 | Adelman . |
| 4,331,480 | 5/1982 | Gutman et al. . |
| 4,374,174 | 2/1983 | Stricklin et al. . |
| 4,472,231 | 9/1984 | Jenkins . |
| 4,499,136 | 2/1985 | Nakamura et al. . |
| 4,533,435 | 8/1985 | Intili . |
| 4,557,966 | 12/1985 | Weil . |
| 4,617,328 | 10/1986 | Liu . |
| 4,631,302 | 12/1986 | Supcoe et al. . |
| 4,752,629 | * 6/1988 | Proudlock et al. .................. 523/122 |
| 4,789,692 | 12/1988 | Rei et al. . |
| 4,824,705 | 4/1989 | Persson et al. . |
| 4,853,297 | 8/1989 | Takahashi et al. . |
| 4,973,448 | 11/1990 | Carlson et al. . |
| 4,983,449 | 1/1991 | Nee . |
| 4,988,236 | 1/1991 | Ramsey . |
| 5,006,185 | 4/1991 | Anthony et al. . |
| 5,104,390 | * 4/1992 | Yum et al. ............................ 604/323 |
| 5,139,700 | 8/1992 | Miksic et al. . |
| 5,209,869 | 5/1993 | Miksic et al. . |
| 5,320,778 | 6/1994 | Miksic et al. . |
| 5,417,676 | * 5/1995 | Wantanabe et al. ................. 604/317 |
| 5,465,527 | 11/1995 | Able . |
| 5,525,426 | * 6/1996 | Kulzick et al. ...................... 428/412 |

FOREIGN PATENT DOCUMENTS

| | | |
|---|---|---|
| 2400663 | 8/1977 | (FR) . |
| 974027 | 3/1979 | (SU) . |

OTHER PUBLICATIONS

Publication—"Synergistic Protection Against Microbiologically Influenced Corrosion Using a 100% Solids Polyurethane Incorporated With Anti–Microbial Agents" Author—Dr. Shiwei Guan Published between Aug., 1997 and Nov. 1997.

* cited by examiner

Primary Examiner—Paul Thibodeau
Assistant Examiner—D. Lawrence Tarazano
(74) Attorney, Agent, or Firm—Robert J. Veal; Robert M. Jackson; Burr & Forman LLP

(57) ABSTRACT

An anti-corrosive material used to protect buried conduits from microbiologically-influenced corrosion, or "MIC". The material preferably comprises a low, medium, or high density polyethylene sleeve having a bactericide impregnated therein such that said bactericide can migrate within the polymer matrix to contact the conduit surface and thereby prevent MIC therein. The material may further comprise a barrier layer of high density polyethylene between the bactericide-containing layer and the environment. The bactericide is able to migrate through the low or medium density polyethylene but the rate of migration of the bactericide is considerably slowed through the high density polyethylene. Thus, the bactericide is substantially prevented from entering the surrounding environment, but rather, is trapped within a "protection zone" adjacent the conduit surface to provide extended protection against microbiologically-influenced corrosion.

10 Claims, No Drawings

PROTECTIVE MATERIAL FOR PREVENTING MICROBIOLOGICALLY-INFLUENCED CORROSION IN BURIED CONDUITS

RELATED MATERIALS

The present application is a continuation-in-part application of pending U.S. patent application Ser. No.08/669,111, filed Jun. 24, 1996, pending, which is incorporated herein by reference.

FIELD OF THE INVENTION

The present invention relates to a protective material for preventing microbiologically-influenced corrosion in buried conduits. More particularly, the present invention relates to a polyethylene sleeve used to encase buried conduits wherein the sleeve has a bactericide impregnated therein to prevent microbiologically-influenced corrosion in the buried conduits.

BACKGROUND OF THE INVENTION

Buried conduits are ubiquitously used for carrying various materials, such as water, natural gas, and sewage. A major problem with buried conduits comprised of metal or concrete with metal reinforcements is corrosion. The severity and rate of corrosion is dependent on the type of material comprising the conduit and the environment in which the conduit is buried. Insuring the longevity of buried conduits is an important part of the infrastructure in the United States and the world. Significant costs are involved in design, development, manufacture, and installation of water, gas, and sewage systems. Failure of these systems from conduit corrosion represents appreciable costs.

The longevity of buried conduits depends on several design and installation features, including resistance to corrosion. There are numerous causes of corrosion, such as oxygen replenishment, presence of sulfides, pH of the surrounding soil environment, stray direct electrical current, and microbiologically-influenced corrosion. In the early 1950's, experimentation was conducted using polyethylene film to encase buried conduits in an effort to prevent corrosion. The results showed that a sleeve of polyethylene film could be easily and quickly slipped over a conduit immediately prior to installation and the sleeve was effective in preventing corrosion, even in severely corrosive soils. Because polyethylene is inexpensive compared to other corrosion abatement systems and is easily applied to conduits, it has become the preferred corrosion abatement system relative to buried conduits.

Polyethylene film is very strong and durable, and can withstand the harsh conditions of burial for an indefinite period. For example, polyethylene sleeves that were installed on buried conduits over 35 years ago, when excavated and examined, exhibited the same physical characteristics they had when first installed. Inspections of field installations years later have confirmed that polyethylene sleeves have generally performed as expected, however, there were some instances of unexplained corrosion. Recent research has shown that colonies of bacteria form on the conduit and their secretions can cause severe corrosion, leading to failure of the buried conduit. The colonies of bacteria consists of both aerobic and anaerobic bacteria, and generally comprise slime-forming, acid-producing, sulfate-producing, nitrate-reducing, iron-oxidizing, and iron-reducing bacteria.

Microbiologically-influenced corrosion ("MIC") from anaerobic sulfate-reducing bacteria ("SRBs") was suspected as the most likely cause of the unexplained corrosion events. The anaerobic bacteria from the genera Desulfovibrio (e.g. *Desulfovibrio desulfuricans*) have been found to be one of the major contributing causes of MIC. However, currently available methods for controlling conduit corrosion do not address microbiologically-influenced corrosion or their application is technically complex and very expensive, or they are not suitable for buried conduits.

SUMMARY OF THE PRESENT INVENTION

It is an object of the present invention to provide an anti-corrosive material which is superior to those presently used to protect buried conduits.

It is another object of the present invention to provide an anti-corrosive material which contains a bactericide to prevent bacterial induced or enhanced corrosion of buried conduits.

It is another object of the present invention to provide an anti-corrosive material which contains a bactericide to prevent bacterial induced or enhanced degradation of the anti-corrosive material.

It is another object of the present invention to provide an anti-corrosive material in the form of a sleeve that can be easily slipped over the candidate conduit without the need for specialized technology or wrapping equipment.

It is another object of the present invention to provide an anti-corrosive material comprising a conduit-contacting layer having a bactericide impregnated therein such that said bactericide can migrate within the conduit-contacting layer to contact the conduit surface and thereby prevent bacterial induced or enhanced corrosion therein.

It is another object of the present invention to provide a multi-layered, anti-corrosive material having a barrier layer adjacent the conduit-contacting layer which prevents the bactericide from penetrating the barrier layer and entering the surrounding environment.

These and other objects of the present invention are accomplished through the use of an anti-corrosive material used to protect buried conduits from microbiologically-influenced corrosion, or "MIC". The material preferably comprises a low, medium, or high density polyethylene sleeve having a bactericide impregnated therein such that said bactericide can migrate within the polymer matrix to contact the conduit surface and thereby prevent MIC therein. The material may further comprise a barrier layer of high density polyethylene between the bactericide-containing layer and the environment. The bactericide is able to migrate through the low or medium density polyethylene but the rate of migration of the bactericide is considerably slowed through the high density polyethylene. Thus, the bactericide is substantially prevented from entering the surrounding environment, but rather, is trapped within a "protection zone" adjacent the conduit surface to provide extended protection against microbiologically-influenced corrosion.

The advantages of the present invention include: (1) no specialized technology is required to apply the polyethylene sleeve as is required with continuous wrapping of the conduit; (2) current installation practices remain unchanged; (3) microbiologically-influenced corrosion is prevented; and (4) applicable industry standards are met without caveat. Thus, the present invention is not limited to simply overcoming the deficiencies of the prior art but introduces enhanced technical advantages in corrosion protection that were not previously available for buried conduits while continuing to meet established industry standards.

These and other objects and advantages of the invention will become apparent from the following detailed description of the preferred embodiment of the invention.

DETAILED DESCRIPTION OF THE PREFERRED EMBODIMENT

The anti-corrosive material of the present invention preferably comprises a polyethylene sleeve conforming to industry standards as described by, but not limited to, the ANSI/AWWA (American National Standards Institute/American Water Works Association) C105/A21.5 published standard, incorporated herein by reference, which describes, inter alia, approved minimum physical and chemical properties for polyethylene sleeves used to protect buried conduits. The ANSI/AWWA standard also defines approved installation procedures for the sleeves. The polyethylene sleeve of the present invention has a bactericide impregnated therein for preventing the growth of certain corrosion-causing bacteria, particularly sulfate-reducing bacteria such as *Desulfovibrio desulfuricans*. The concentration of the bactericide is preferably between about 0.05% to about 5.0% by weight of the material, although this can vary depending on the type of bactericide used and the environment in which it will be used. The sleeves of the present invention find particular application in preventing microbiologically-influenced corrosion (MIC) in conduits comprised of metal, including ductile iron pipe (DIP), or concrete with metal reinforcements.

To prepare the anti-corrosive material, the bactericide is blended with molten polyethylene resin. The polyethylene is preferably low or medium density, although high density polyethylene may be used as well. The bactericide must be able to withstand the temperatures required to melt and process the polyethylene. The polyethylene and bactericide are typically mixed at about 400° F.; however, the temperature normally should not exceed about 425° F. because the bactericide may begin to denature or evaporate. After the polyethylene and bactericide are adequately mixed, the molten mixture is extruded to form a polyethylene sleeve. The process of extruding (or calendering, etc.) polyethylene films is well known in the art and will not be described herein. The bactericide is partially bound to the polyethylene matrix such that some bactericide is retained within the polymer matrix to prevent bacterial growth and degradation thereof, while unbound bactericide can slowly migrate through the polymer matrix to the surface of the conduit to prevent bacterial growth thereon.

Bactericides which preliminary studies have indicated will adequately kill corrosion-causing bacteria and which can be successfully incorporated within the polyethylene sleeve include the following:

| Chemical Name | Brand Name/Source |
|---|---|
| 1. Bromonitropropanediol | ULTRA FRESH ®-SAB Thomson Research Associates (Toronto, Ontario, Canada) |
| 2 Organotin | ULTRA FRESH ®-DM50 Thomson Research Associates (Toronto, Ontario, Canada) |
| 3. 2,4,4'-Trichloro-2'-Hydroxy diphenyl ether | ULTRA FRESH ®-NM100 Thomson Research Associates (Toronto, Ontario, Canada) |
| 4. Diiodomethyl-p-tolyl sulfone | ULTRA FRESH ®-95 Thomson Research Associates (Toronto, Ontario, Canada) |

An alternate embodiment of the present invention comprises a multi-layered, co-extruded polyethylene sleeve having at least two layers: a conduit-contacting layer preferably comprising a low or medium density polyethylene impregnated with a bactericide, and a barrier layer preferably comprising a high density polyethylene to provide a barrier between the conduit-contacting layer and the environment. The bactericide is able to migrate through the low or medium density polymer matrix but the rate of migration of the bactericide is considerably slowed through the high density polymer. Thus, the bactericide is substantially prevented from entering the surrounding environment, but rather, is trapped within a "protection zone" adjacent the conduit surface to provide extended protection against microbiologically-influenced corrosion. The process of co-extruding (or calendering, laminating, etc.) multi-layered films is well known in the art and will not be described herein.

It is important to note that the anti-corrosive material may be comprised from only one layer of polyethylene having the bactericide impregnated therein to a material having a plurality of layers with any number of layers having the bactericide impregnated therein. Further, while polyethylene is preferred because it is a standard in the industry, other materials may be substituted therefor without departing from the spirit of the invention, which is the incorporation of bactericide into conduit sleeves for protecting the buried conduits from microbiologically-influenced corrosion. Further, other effective bactericides may be substituted for those listed above; however, they must be able to endure the temperatures required for mixing with the polyethylene.

It is to be understood that the form of the invention shown is a preferred embodiment thereof and that various changes and modifications may be made therein without departing from the spirit of the invention or scope as defined in the following claims.

What is claimed is:

1. An apparatus for carrying fluids wherein said apparatus is resistant to microbiologically-influenced corrosion, said apparatus comprising a conduit comprising a material selected from the group consisting of metal and concrete with metal reinforcements; and a sleeve for encasing said conduit wherein said sleeve has a bactericide impregnated therein for killing corrosion-causing bacteria, said bactericide selected from the group consisting of bromonitropropanediol, 2,4,4'-trichloro-2'-hydroxy diphenyl ether, and diiodomethyl-p-tolyl sulfone.

2. An apparatus according to claim 1 wherein said conduit comprises ductile iron pipe.

3. An apparatus according to claim 1 wherein said sleeve comprises a material selected from the group consisting of low density, medium density, and high density polyethylenes.

4. An apparatus according to claim 1 wherein said bactericide is between 0.05% to 5% by weight of said sleeve.

5. An apparatus according to claim 1 wherein said sleeve comprises a first layer contacting said conduit and having said bactericide impregnated therein for killing corrosion-causing bacteria, and a second layer having a permeability resistant to the migration of said bactericide for maintaining said bactericide in a protection zone proximate said conduit.

6. A protective material for preventing microbiologically-influenced corrosion in buried conduit comprising a material selected from the group consisting of metal, and concrete with metal, said protective material comprising a sleeve for encasing said conduit wherein said sleeve has a bactericide impregnated therein for killing corrosion-causing bacteria, said bactericide being selected from the group consisting of bromonitropropanediol, 2,4,4'-trichloro-2'-hydroxy diphenyl ether, and diiodomethyl-p-tolyl sulfone.

7. A protective material according to claim 6 wherein said conduit comprises ductile iron pipe.

8. A protective material according to claim 6 wherein said sleeve comprises a material selected from the group consisting of low density, medium density, and high density polyethylenes.

9. An apparatus according to claim 6 wherein said bactericide is between 0.05% to 5% by weight of said sleeve.

10. A protective material according to claim 6 wherein said sleeve comprises a first layer for contacting said conduit and having said bactericide impregnated therein for killing corrosion-causing bacteria, and a second layer having a permeability resistant to the migration of said bactericide for maintaining said bactericide in a protection zone proximate said conduit.

* * * * *